United States Patent [19]

van den Berg

[11] 4,178,300

[45] Dec. 11, 1979

[54] SOLUTIONS OF ORGANIC MAGNESIUM COMPOUNDS CONTAINING OXYGEN IN HYDROCARBONS

[75] Inventor: Cornelis E. P. V. van den Berg, Geleen, Netherlands

[73] Assignee: Stamicarbon, B.V., Geleen, Netherlands

[21] Appl. No.: 957,002

[22] Filed: Oct. 31, 1978

[30] Foreign Application Priority Data

Oct. 31, 1977 [NL] Netherlands .......................... 7711923

[51] Int. Cl.² .......................... C11C 1/00; C07C 51/00; C07C 27/00
[52] U.S. Cl. ................................ 260/413; 260/593 R; 568/716; 568/807; 568/840; 568/851; 568/902; 562/405; 562/493; 562/512
[58] Field of Search ............ 260/413 R, 413 S, 593 R; 568/851, 902, 716, 840, 807; 562/405, 493, 512

[56] References Cited

U.S. PATENT DOCUMENTS

| | | | |
|---|---|---|---|
| 2,287,088 | 6/1942 | Cohen | 568/815 |
| 2,570,058 | 10/1951 | Hunter | 568/815 |
| 2,593,314 | 3/1952 | Kimberlin | 568/815 |

*Primary Examiner*—John F. Niebling
*Attorney, Agent, or Firm*—Cushman, Darby & Cushman

[57] ABSTRACT

A novel process is described for the preparation of novel organic solutions of organooxy magnesium compounds of low viscosity, which solutions are formed in the presence of at least 5 mol % based on the magnesium compound of an organooxy compound of a transition metal of Groups IV through VI of the Periodic Table.

17 Claims, No Drawings

SOLUTIONS OF ORGANIC MAGNESIUM COMPOUNDS CONTAINING OXYGEN IN HYDROCARBONS

The invention relates to a process for the preparation of solutions of organooxymagnesium compounds, i.e., organic magnesium compounds wherein the organic radical is linked to the magnesium atom through an oxygenation—in particular solutions of hydrocarbyloxy magnesium compounds.

It should be noted that metal compounds, especially magnesium compounds, in which an organic group is attached to the metal atom through a carbon atom, are called organometallic compounds, i.e., organomagnesium compounds, and such compounds should not be confused with the organooxy metal compounds meant herein.

In this invention, the organic radicals attached to the magnesium atom through an oxygen atom may either be saturated or unsaturated, with straight or branched chains, or they may be cyclic, and are preferably hydrocarbon radicals. These radicals may be attached to magnesium at any carbon atom of the chain through an oxygen atom. These radicals may, however, also contain additional hetero atoms, such as oxygen, sulphur, nitrogen, phosphorus, or halogen, but preferably these radicals do not contain hetero atoms, other than one or more oxygen atoms. Examples are particularly hydrocarbyl radicals attached by way of an oxygen atom, such as alkyl or cycloalkyl groups or the related mono-unsaturated or polyunsaturated groups derived therefrom, aryl groups, alkaryl or aralkyl groups, or hydrocarbyl groups substituted by one or more hydroxy, oxo (i.e., with one or more terminal or non-terminal carbonyl groups), and/or carboxyl groups. In the present invention the term "organooxymagnesium compounds" especially denotes the hydrocarbyloxymagnesium compounds such as alkoxides, magnesium aroxides (i.e., derivatives of phenol or homologues of phenol), magnesium carboxylates (i.e., the magnesium salts of carboxylic acids, both aliphatic and aromatic), and magnesium chelates of 1,3-diketones (in particular the magnesium acetyl acetonate). The organic magnesium compounds containing oxygen are preferably magnesium alkanolates.

Magnesium alkanolates and their preparation have long been known. According to Gmelin's Handbuch der Anorganischen Chemie, Edition 8 Magnesium, System No. 27, Volume A, pp. 315 and 316, it was already known at the turn of the century that magnesium dissolves in absolute methanol at room temperature to form magnesium methylate. The reaction with ethanol has been found to be more difficult, and the reaction with propanol or higher alcohols very difficult, (e.g., generally requiring reaction in the gaseous phase with heated magnesium, and even no reaction takes place sometimes). Methods for preparing and forming magnesium alkanolates have also been described in Beilstein's Handbuch der Organischen Chemie under the entries methanol, ethanol, propanol, isopropanol and higher alcohols (see system numbers 19, 20 and 24 in the main and the supplementary volumes).

Magnesium methanolate is fairly soluble in methanol; magnesium ethanolate is appreciably less so in ethanol. As the number of carbon atoms in the alkoxy groups increases, the solubility in the corresponding alcohol rapidly decreases further. Indeed, magnesium propylate or isopropylate is virtually insoluble in the corresponding alcohol.

According to U.S. Pat. No. 2,570,058, magnesium alkanolates can be formed by reaction with alkanols with at least 4 carbon atoms if this conversion is effected in the presence of chloroform or carbon tetrachloride and with a catalytic amount of mercury compound. If the conversion of magnesium with, e.g., n-amyl alcohol is attempted in the presence of a small amount of mercury compound, but in the absence of chloroform or carbon tetrachloride, the reaction soon stops and a deposit can be observed on the surface of the magnesium metal. However, if the conversion is effected with a mixture of 95% of n-amyl alcohol and as little as 5% of carbon tetrachloride and with a catalytic amount of a mercury compound, the reaction can proceed until the magnesium has dissolved completely. The chlorine compound obviously has a solubilizing effect, which can also be observed when a mixture of an alcohol and a hydrocarbon solvent is used. However, nothing is stated about the solubility of the materials in hydrocarbons.

Magnesium aroxides, especially magnesium phenolate, are also well-known compounds. Magnesium phenolate can be prepared in an aqueous medium from phenol and magnesium oxide or magnesium hydroxide.

Of the magnesium chelates of 1,3-diketones, magnesium acetyl acetonate is mentioned in particular, and can be prepared by conversion of acetyl acetonate with magnesium carbonate in water or with magnesium oxide in alcohol. As stated in applicant's earlier Netherlands Patent Application No. 70 17569, (see U.S. Ser. Nos. 203,429, now abandoned, 501,616, now abandoned and 735,440) magnesium alkanolates as such are generally not soluble in hydrocarbons or can be dissolved only with the formation of very viscous solutions. Said application also mentions some measures to obtain less viscous solutions. (It has been supposed, although this must not be considered a statement binding upon the present applicant, that some sort of magnesium polymers are present in the viscous liquids, as described by Bryce-Smith, and Wakefield in J. Chem. Soc. 1964 (July) 2483–5.

The abovementioned patent applications and the prior art do not, however, describe a straightforward method for dissolving organooxy magnesium compounds to obtain non-viscous solutions and the methods which are described therein give less than favorable results in a number of cases. However, it is highly desirable to prepare solutions of organooxy magnesium compounds of low viscosity for use in catalyst systems.

By the present invention, it has now been found that solutions of organooxy magnesium compounds of desirably low viscosity can be prepared by dissolving in a hydrocarbon solvent a magnesium compound of this type (in particular a compound in which each of the two organo radicals attached to magnesium by way of an oxygen atom contains 3 to 30 carbon atoms, and the two together contain at least 7 carbon atoms), in the presence of at least 5 moles percent, calculated to the magnesium compound, of an organooxy compound of a transition metal from Groups IV through VI of the Periodic Table. Magnesium alkanolates with 3 to 30 carbon atoms per alkoxy group and at least 7 carbon atoms in the two alkoxy groups can thus be dissolved in a hydrocarbon solvent, preferably with gentle heating, while an organic compound of a transition metal containing oxygen is added.

Heating is generally effected at at least 50° C. and, preferably, at least 70° C. Use of solvents with low boiling points, such as propane, butane, pentane dictates effecting the process under pressure. When such low boiling solvents are not preferred, solvents with higher boiling points will preferably be chosen whereby the process may be effected at an atmospheric pressure. Advantageously, the dissolving can be effected with gentle heating under reflux.

When hydrocarbons or hydrocarbon fractions with higher boiling points are used as the solvent, higher temperatures, e.g., of over 100° or even 200° C. may also be used, which sometimes is found to be advantageous and which, will generally increase the rate of conversion and dissolution. For economical reasons, of course, heating will generally not be done at a higher temperature than is required for smooth dissolution.

Although the magnesium alkanolates of the lower alcohols can be prepared directly from magnesium and the corresponding alcohol, the preparation of magnesium alkanolates with alkoxy groups with 5 or more carbon atoms must generally start from magnesium alkanolates of the lower alcohols, e.g., magnesium methanolate, magnesium ethanolate or magnesium isopropanolate, and then heating the same with a higher alcohol, e.g., hexanol, octanol, decanol, etc., to convert them into the magnesium alkanolate of the higher alcohol, while the lower alcohol is liberated—i.e., a transalkanolation.

A disadvantage of these conversions is that the removal of the released lower alcohol from the reaction mixture is usually highly incomplete, and thus the reaction proceeds only incompletely. For instance, when magnesium isopropanolate is heated in a hydrocarbon solvent with an amount of decanol that can replace one or both isopropoxy groups, the isopropanol which is liberated, can at first be removed from the reaction mixture by boiling. Before long, however, a very viscous solution of magnesium isopropanolatedecanolate and/or of magnesium didecanolate in the hydrocarbon solvent will be formed. Isopropanol can no longer be removed from this very viscous mass by boiling and the conversion thus cannot be continued to completion. Therefore, to prepare the magnesium didecanolate, a great excess of decanol may be added, if so desired, and the reaction can then be carried on to completion as a result of the strong dilution. But, the replacement of the excess decanol by a hydrocarbon solvent, which usually has a lower boiling point than decanol (231° C.), is then itself both cumbersome and expensive.

The present process is particularly suitable for the direct preparation, from a magnesium alkanolate having 1 to 3 carbon atoms in the alkoxy groups, of a magnesium alkanolate having a higher number of carbon atoms in the alkoxy groups, by adding a transition-metal compound containing organooxy radicals, e.g., a tetraalkoxy titanium compound, during the conversion of the magnesium alkanolate with 1 to 3 carbon atoms with the higher alkanol, e.g., an alkanol with from 4 to 30 carbon atoms.

If magnesium isopropanolate, together with e.g., 20 moles % of tetrabutoxy titanium, with respect to the amount of magnesium, and one or two equivalents of decanol, is introduced into an organic solvent, and the mixture is heated, a desirably low-viscosity solution of magnesium isopropanolatedecanolate, and/or of magnesium didecanolate, is formed, from which the liberated isopropanol can now readily be evaporated so as to achieve substantially full completion of the reaction.

The solvent chosen for this conversion reaction is preferably one that can easily be separated from isopropanol by distillation. The solvent used, and the final solution, must not itself contain more than only a small amount of organo oxygen compounds, such as the lower alcohol released in the conversion to a magnesium higher alcoholate. As a minimim, the amount of oxygen in such solvent compounds must be less than the amount of oxygen present in the organooxy radicals attached to the metal. Such oxo compounds are, however, preferably entirely absent, and effective separation of the resulting alcohol and hydrocarbon solvent is therefore desirable.

What has been said above by way of example regarding the conversion of magnesium isopropanolate with decanol naturally also applies to the conversion of any other magnesium lower alkanolate of an alkanol with at most 3 carbon atoms to a higher alkanol, magnesium alkanolate, i.e., one with a hydrocarbyloxy radical having from 4 to 30 carbon atoms.

While magnesium alcoholates can be prepared directly from butanol or pentanol, and these can then be converted with higher alcohols in a similar way, a process of this type is of little attractiveness. It is much easier to proceed by preparing a methanolate, ethanolate, propanolate or isopropanolate and hence use these as starting materials for the prepration of a magnesium alkanolate of a higher alkanol. The preparation of magnesium butanolate or pentanolate is also easier by way of the conversion of the magnesium compound of a lower alcohol than by the direct route. Hence, the preparation via a lower alkanolate is also to be preferred in these cases.

By preference, one of the alkoxy groups of the magnesium alkanolate to be dissolved should contain at least 5 carbon atoms, for the solubility is improved as the number of carbon atoms in the alkoxy groups is greater. Without the transition metal compounds, however, very viscous solutions, or even solid gels, that are very difficult or impossible to handle or process are generally obtained at concentrations as low as less than 0.5 molar, e.g., only 0.1 or 0.2 M.

In general, however, solutions of magnesium alkanolates in which different alkoxy groups are attached to the magnesium are less viscous than when the alkoxy groups are the same. Consequently, magnesium alkanolates with different alkoxy groups are to be preferred.

These solutions of mixed alkanolates can also be prepared by heating a mixture of a magnesium alkanolate, having a smaller alkoxy group, and a magnesium alcoholate having a higher alkoxy group, such as, e.g., heating together magnesium diisopropanolate and magnesium didecanolate.

The term "organooxy transition-metal compounds" as used herein denotes compounds of transition metals from the Groups IV through VI in which organic groups, preferably hydrocarbyloxy radicals, are attached to the transition metal by way of an oxygen atom. These include the alkoxides or alkanolates, the aroxides, particularly the phenolates, the alkane carboxylates, and also the transition-metal chelates of 1.3-diketones, particularly of acetyl acetone. The organic radical attached to a transition-metal atom by way of an oxygen atom contain from 1 to 20 preferably from 4 to 8 carbon atoms per radical. Use is preferably made of alkanolates of transition metals. Suitable transition-metal compounds are the titanium, zirconium, vanadium and chromium compounds, but the titanium compounds are used by preference. Of the titanium compounds, titanium tetrabutanolate (or tetrabutoxy titanium, abbreviated TBT in most cases) is to be preferred.

The at most slightly viscous solutions provided according to this invention can be obtained by first dissolving a magnesium alkanolate in a hydrocarbon solvent which will itself produce a very viscous solution. Next, a transition metal compound is added, after which the viscosity is then very substantially decreased. Naturally only those magnesium alkanolates that are soluble as such in hydrocarbons can be used for this purpose. The magnesium alkanolate is preferably dissolved in the presence of a transition-metal compound.

The amount of transition-metal compound used amounts to at least 5 mol % calculated to the magnesium compound and, essentially, has no upper limit. For practical reasons, however, the amount of transition-metal compound will not be chosen too large, and will preferably not be greater than necessary to achieve the desired solution. Above a certain concentration level of the transition-metal compound, which depends on the particular conditions, the viscosity of the solution of the magnesium compound will not be further reduced, and, consequently, greater amounts of the transition metal compound need not generally be used. The amount of transition-metal compound which will give the best results in a given case can readily be determined by simple experiment.

The efficacy of the transition-metal compounds for this invention also depends somewhat on the particular transition-metal and the organic radicals thereon. Titanium compounds are very effective, but with zirconium alcoholates clearly relatively larger amounts are required. In general, however, an amount of less than 100 moles % of transition-metal compound calculated to the magnesium compound will suffice. Use is preferably made of at most 60 mol % and, more in particular, at most about 35 mol %. The best results, i.e., the least viscous solutions with the smallest amount of transition metal, are obtained with titanium tetraalcoholates. Use of only 5 mol % can produce solutions that can well be handled, even though they may still be slightly viscous. At temperatures below room temperature, especially below 0° C., which may occur during storage in the open air in moderate climates, solutions of this type can, however, become very viscous. At least 15 moles % of titanium alcoholate will then preferably be used in order to prepare solutions that remain of low viscosity even upon prolonged storage at temperatures of, e.g., −10° C. To promote effectiveness, such titanium tetra-alcoholates will be used in amounts not exceeding 60 mol %, and by preference in amounts not exceeding 35 mol %. Compounds of other transition metals generally require the use of larger amounts.

The hydrocarbons used as the solvent in the present invention are aliphatic or cycloaliphatic hydrocarbons, such as, e.g., propane, butane, isobutane, one or more pentanes, hexanes, heptanes, etc., cyclopentane, cyclohexane, and homologues thereof, etc. Aromatic hydrocarbons, too, can well be used as solvents, but aliphatic or cycloaliphatic hydrocarbons are to be preferred for practical reasons.

Lower hydrocarbons, such as propane and butane, can be used only under pressure. Use is preferably made of solvents that are liquid at atmospheric pressure.

Use may also be made of petroleum fractions that consist of aliphatic and cycloaliphatic hydrocarbons and may contain widely varying amounts of aromatics. By preference, hydrocarbon fractions with too high boiling points are not chosen, as they become ever more viscous with higher molecular weight. The upper limit of the solvent boiling range should therefore be below 300° C. and preferably below 200° C., and, even more preferred, below about 120° C. The organooxy magnesium compounds in solutions in hydrocarbons, especially the magnesium alcoholates, can be used, for instance, as catalyst components and in organic syntheses, e.g., in the polymerization of lower alkenes.

The invention will now be further elucidated by the following examples, without, however, being restricted to these specific embodiments.

EXAMPLE 1

Preparation of a solution of $Mg(OC_{10}H_{21})_2$.

48 grams of magnesium cuttings and a pinch of iodine are placed in a 2-liter three-necked flask provided with a stirrer and a reflux condenser. Next, 0.5 liter of absolute methanol is added dropwise.

The reaction proceeds vigorously and a viscous white mass is formed. Excess decanol-1 (0.5 l.) is then added and the mixture is stirred at 70° C. for three hours. The alcohol is evaporated in vacuo and a grey solid mass is obtained. Now, 1.5 liter of dry gasoline and 0.2 mole (68 ml) of tetrabutoxy titanium are added. The solid mass dissolves completely upon stirring at 70° C. When cooled to room temperature, the resulting solution remains thin, freely mobile and of low viscosity.

EXAMPLE 2

Preparation of a solution of $Mg(-O-iC_3H_7)(OC_{10}H_{21})$.

250 ml of gasoline, 40 mmoles (4.56 g) of magnesium ethanolate, 40 mmoles (3.1 ml) of isopropanol and 40 mmoles (7.6 ml) of decanol-1 are placed in a 0.5-liter three-necked flask provided with a stirrer, a reflux condenser and gas and liquid inlets.

The mixture is kept at 70° C. for 48 hours with stirring, while dry nitrogen is passed over the reaction mixture. The gas-vapor flow is discharged through the condenser that is slightly cooled with air and the evaporated gasoline is regularly made up. The insoluble magnesium ethanolate slowly dissolves with the formation of magnesium isopropanolate decanolate. The ethanol liberated is discharged as a vapor together with the nitrogen passed over and the gasoline vapor. A viscous gel is, however, then formed.

4 mmoles (1.36 ml) of tetrabutoxy titanium are then added. The viscous gel now gradually becomes less viscous and after 1 hour at 70° C. a thin, slightly turbid solution of low viscosity has formed.

EXAMPLE 3

Preparation of a solution of $Mg(OC_{10}H_{21})(OC_{16}H_{33})$.

8.6 grams (75 mmoles) of magnesium ethanolate in 250 ml of pentamethyl heptane are placed in a 500-ml three-necked flask provided with a stirrer, reflux condenser and gas and liquid inlets. 22.1 ml of cetyl alcohol (hexadecanol-1,$C_{16}H_{33}OH$) are added and heating is effected at 110° C. while nitrogen is passed over. After 1 hour 14.3 ml of decanol-1 are added and the solution is stirred at 110° C. for 4 hours while nitrogen is passed over continuously.

A viscous mass with gel-like particles is obtained.

7.5 mmoles (2.6 ml) of tetrabutoxy titanium are then added. The viscous reaction mixture soon becomes less viscous and after one hour the solution is then, freely mobile and it remains so upon cooling to room temperature.

EXAMPLE 4

Preparation of a solution of Mg(—O—iC$_3$H$_7$)(OC$_{10}$H$_{21}$).

76 mmoles (10.8 g) of magnesium diisopropanolate, 76 mmoles (14.5 ml) of decanol-1 and 250 ml of gasoline are placed in a 0.5 liter three-necked flask provided with a stirrer, a reflux condenser and gas and liquid inlets. The mixture is heated with stirring and kept at 70° C. for 4 hours, while a small flow of nitrogen is passed over. The nitrogen laden with isopropanol vapor and gasoline vapor is discharged through the condenser that is cooled slightly with air. The evaporated gasoline is made up at intervals. A highly viscous solution is obtained.

After 7.6 mmoles (2.6 ml) of tetrabutoxy titanium are added, the solution is kept at 70° C. The solution now becomes less viscous and after being stirred at 70° C. for 1 hour it is as thin and mobile as water and it stays so upon cooling to room temperature.

COMPARATIVE EXPERIMENT

Instead of tetrabutoxy titanium, 76 mmoles of aluminum triisopropanolate are added to the viscous solution of magnesium isopropanolate decanolate prepared according to Example 4. The viscosity of the solution did not change after 1 hour's stirring at 70° C.

EXAMPLE 5

Preparation of a solution of Mg(—O—iC$_3$H$_7$)(OC$_{10}$H$_{21}$).

72 mmoles (10.2 grams) of magnesium isopropanolate in 250 ml of gasoline and 14.4 mmoles (4.9 ml) of tetrabutoxy titanium are placed in a 0.5-liter three-necked flask provided with a stirrer, a reflux condenser and gas and liquid inlets. This mixture is kept at 70° C. for 8 hours with stirring, while nitrogen is passed over. It is found that the magnesium isopropanolate does not dissolve and no change is observed in the system.

72 mmoles (13.7 ml) of n.decanol are then added and the mixture is stirred at 70° C. for another 8 hours while nitrogen is passed over. The evaporated gasoline is made up at intervals. A clear solution is thus formed, which also remains as water upon cooling to room temperature. This solution is still found to be comparably thin after three months storage at −7° C.

EXAMPLE 6

Preparation of a solution of Mg(—O—i—C$_3$H$_7$)(OC$_8$H$_{17}$).

The process of Example 4 is carried out, but 76 mmoles of n-octanol-1 are now added in place of decanol-1. Here, too, a solution is obtained that is thin at room temperature and the viscosity of which has not changed upon 10 weeks storage at room temperature.

EXAMPLE 7

Preparation of a solution of Mg(—O—iC$_3$H$_7$)(2—OC$_8$H$_{17}$).

Example 6 is repeated on the understanding that 76 mmoles of octanol-2 are added. A thin solution is obtained which also stays upon cooling to room temperature and which is distinguished from the solution obtained in Example 6 only by a slight turbidity.

EXAMPLE 8

Preparation of Mg(OC$_{10}$H$_{21}$)$_2$.

76 mmoles (10.8 g) of magnesium diisopropanolate, 152 mmoles (28.9 ml) of decanol-1 and 250 ml of gasoline are placed in a 0.5-liter three-necked flask provided with a stirrer, a reflux condenser and gas and liquid inlets. Next, 7.6 mmoles (2.6 ml) of tetrabutoxy titanium are added. The reaction mixture is heated to 70° C. with stirring and kept at this temperature for 4 hours. A small flow of nitrogen is passed over the mixture and the nitrogen laden with isopropanol vapor and gasoline vapor is discharged through the condenser that is slightly cooled with air. The evaporated gasoline is made up at intervals. A thin solution is obtained which remains invariably thin after cooling and 10 weeks storage at room temperature.

EXAMPLE 9

Preparation of a solution of Mg(—O—iC$_3$H$_7$)(OC$_6$H$_{13}$).

A solution is prepared in the same way as in Example 4, but 76 mmoles of hexanol-1 are added instead of decanol-1. A very viscous solution is obtained already after 1 hour's stirring at 70° C. Then, 7.6 mmoles (2.6 ml) of tetrabutoxy titanium are added and the solution becomes as thin as water after 1 hour at 70° C. The solution remains thin upon cooling and storage at room temperature.

EXAMPLE 10

Preparation of a solution of Mg(—O—iC$_3$H$_7$)(OC$_5$H$_{11}$).

A solution is prepared in the same way as in Example 4, but 76 mmoles of pentanol-1 are added instead of decanol-1. After 1 hour's stirring at 70° C. a viscous solution is obtained, the viscosity of which increases further when stirring at 70° C. is continued.

After 3 hours 7.6 mmoles (2.6 ml) of tetrabutoxy titanium are added. The solution then becomes as thin as water after about 10 minutes. The solution remains thin at room temperature, but it gradually becomes slightly more viscous upon prolonged storage at room temperature.

EXAMPLE 11

Preparation of a solution of Mg(—O—iC$_3$H$_7$)(OC$_{10}$H$_{21}$).

A solution of Mg(—O—iC$_3$H$_7$)(OC$_{10}$H$_{21}$) is prepared in the same way as in Example 4, but 250 ml of cyclohexane are used as the solvent instead of 250 ml of gasoline.

A thin solution is obtained, which also remains thin upon cooling and after prolonged storage at room temperature.

EXAMPLE 12

Preparation of Mg(—O—iC$_3$H$_7$)(OC$_{10}$H$_{21}$).

Example 4 is repeated, but 7.6 mmoles of tetrabutoxy zirconium are added instead of tetrabutoxy titanium. After 1 hour's stirring at 70° C. the viscosity of the solution has decreased appreciably, but the solution has not become thin. Another 7.5 mmoles of tetrabutoxy zirconium are added and a thin solution is now obtained after 1 hour's stirring at 70° C.

After cooling and three days storage at room temperature the viscosity has clearly increased, although the solution can still be handled well.

Again, 7.6 mmoles of tetrabutoxy zirconium are added (so in all 22.8 mmoles, i.e., 30 moles %). The solution then obtained remains permanently thin.

EXAMPLE 13

Preparation of a solution of Mg(—O—iC$_3$H$_7$) (OC$_{10}$H$_{21}$).

A solution is prepared by the process of Example 4, but only 3.8 mmoles of tetrabutoxy titanium are added (i.e., just 5 mol % based on magnesium). The viscous solution of magnesium isopropylate decanolate becomes thin after 1 hour's stirring at 70° C. but upon cooling to room temperature this solution did become viscous.

EXAMPLE 14

Preparation of a solution of Mg(OOCC$_{17}$H$_{35}$)$_2$.

24.3 grams (75 mmoles) of magnesium stearate and 250 ml of pentamethylheptane are placed in a 0.5-liter three-necked bottle provided with a stirrer and a reflux condenser. The mixture is heated at 150° C. with stirring, whereupon the magnesium stearate is dissolved in the pentamethyl heptane to form a clear but jelly-like viscous solution.

2.6 ml (7.5 mmoles) of tetrabutoxy titanium are now added. The viscosity of the jelly is considerably lowered. Cooling to room temperature again gives rise to a viscous gel. The gel is heated again to 150° C. with stirring and another 2.6 ml (7.5 mmoles) of tetrabutoxy titanium are added. The viscous solution now becomes thin and stays so upon cooling to room temperature. The solution is allowed to stand at room temperature for 7 days. The viscosity is found to increase somewhat, but the solution can still be handled very well.

In the foregoing description of this invention, the term 'low viscosity' used in describing the novel solutions hereby obtained is, of course, used in contrast to the gel or jelly-like consistency of the organooxy magnesium solution characteristically obtained when the inventive process is not employed. The low viscosity solutions provided by this invention will in many cases have liquid flor or pouring or draining characteristics comparable to that of e.g., water or liquid hydrocarbons or, for instance, of halogenated lower alkyl hydrocarbon solvents, as observed at ambient temperatures. For instance, addition of no or only 4 moles-% tetrabutoxy titanium to a 0.3 molar Mg (O—iC$_3$H$_7$) (OC$_{10}$H$_{21}$)-solution forms a viscous jelly, of which the viscosity cannot be determined. By addition of 10 moles-%, 20 moles-% and 30 moles-% of tetrabutoxytitanium, calculated to the magnesium compound, the viscosity of the solution becomes successively 13, 0.8 and 0.7 mPa.s at 25° C., which values are comparable with the viscosity of benzene or gasoline being 0.7 respectively 0.5 mPa.s.

Thus, the low viscosity organooxy magnesium compounds solutions developed by this invention are capable of being easily handled and transported through lines, pipes, tubes and the like apparatus, via conventional pumping devices as are normally used in chemical process technology for transporting liquids, and in sharp contrast to what would otherwise be the requirements for and difficulty in similarly transporting a gel.

What is claimed is:

1. A process for the preparation of low viscosity solutions of organooxy magnesium compounds, in which the organic radicals attached to magnesium by way of an oxygen atom contain from 3 to 30 carbon atoms each, and together at least 7 carbon atoms, which consists essentially in dissolving said compound in a hydrocarbon solvent in the presence of at least 5 mol %, calculated to the magnesium compound, of an organooxy transition metal compound from Groups IV through VI of the Periodic Table.

2. The process of claim 1, wherein a magnesium compound is dissolved wherein the organic radicals attached by way of an oxygen atom contain only carbon, hydrogen and oxygen atoms.

3. Process according to claim 2, wherein hydrocarbyloxy radical, are attached to magnesium by way of oxygen atoms.

4. Process according to claim 3, wherein a magnesium dialkanolate is dissolved.

5. Process according to claim 4, wherein a magnesium dialkanolate with different alkoxy groups is dissolved.

6. Process according to claim 2, wherein the magnesium compound used is a magnesium salt of an aliphatic carboxylic acid.

7. Process according to any one of claims 1 to 6, wherein the dissolution is effected with heating.

8. A process according to claim 1, wherein a solution of a magnesium alkanolate with from 3 to 30 carbon atoms per alkoxy group, and together at least 7 carbon atoms, is prepared by first converting a magnesium alkanolate with from 1 to 3 carbon atoms per alkoxy group by transalkanolation with from 1 to 2 equivalents of an alkanol having from 3 to 30 carbon atoms in the presence of at least 5 moles-% calculated to the magnesium compound from Groups IV through VI of the Periodic Table.

9. Process according to claim 8, wherein a solution of a magnesium alkanolate is prepared in which at least one alkoxy group contains at least 5 carbon atoms.

10. Process according to any one of claims 1 to 6, 8 or 9, wherein use is made of a compound of a transition metal from Groups IV through VI in which hydrocarbyloxy groups with from 1 to 20 carbon atoms are attached to the transition-metal atom by way of an oxygen atom.

11. Process according to claim 10, wherein use is made of a transition-metal alkanolate.

12. Process according to claim 11, wherein use is made of a titanium alkanolate.

13. Process according to claim 12, wherein tetrabutoxy titanium is used.

14. Process according to claim 1, wherein at least 15 moles-% of transition-metal compound calculated to magnesium is used.

15. Process according to claim 1, wherein at most 100 moles % of transition-metal compound calculated to magnesium is used.

16. Process according to claim 15, wherein at most 60 moles % of transition-metal compound, calculated to magnesium, is used.

17. A thin solution of low viscosity of a magnesium alkanolate having from 3 to 30 carbon atoms per alkoxy group, and together at least 7 carbon atoms, in a hydrocarbon solvent, and containing at least 5 mol %, calculated to magnesium, of a hydrocarbyloxy-compound of a transition metal from Groups IV through VI of the Periodic Table.

* * * * *